US00PP12020P2

(12) United States Plant Patent
Rother

(10) Patent No.: US PP12,020 P2
(45) Date of Patent: Jul. 31, 2001

(54) DIMORPHOTHECA PLANT NAMED 'PURPLE BLUSH'

(76) Inventor: Reinhard W. Rother, P.B. 327, Emerald, Victoria (AU)

( * ) Notice: Subject to any disclaimer, the term of this patent is extended or adjusted under 35 U.S.C. 154(b) by 0 days.

(21) Appl. No.: 09/545,906

(22) Filed: Apr. 9, 2000

(51) Int. Cl.[7] ..... A01H 5/00
(52) U.S. Cl. ..... Plt./263
(58) Field of Search ..... Plt./263, 360

*Primary Examiner*—Bruce R. Campell
*Assistant Examiner*—Kent L. Bell
(74) *Attorney, Agent, or Firm*—C. A. Whealy

(57) ABSTRACT

A distinct cultivar of Dimorphotheca plant named 'Purple Blush', characterized by its upright and mounding growth habit; dark green leaves; freely branching habit; white ray florets with purple bases which gives the appearance of a purple ring at the center of the inflorescence; numerous inflorescences per plant; and relative tolerance to high temperatures.

1 Drawing Sheet

BACKGROUND OF THE INVENTION

The present Invention relates to a new and distinct cultivar of Dimorphotheca plant, botanically known as *Dimorphotheca aurantiaca*, and referred to by the cultivar name 'Purple Blush'.

The new cultivar is a product of a planned breeding program conducted by the Inventor in Emerald, Victoria, Australia. The objective of the breeding program was to create new Dimorphotheca cultivars with large inflorescences and attractive ray floret colors.

The new cultivar originated from a cross made by the Inventor of a proprietary selection of *Dimorphotheca aurantiaca* identified as code No. 92/18 as the female, or seed, parent and a proprietary selection of *Dimorphotheca aurantiaca* identified as code No. 93/94, as the mole, or pollen, parent. The new Dimorphotheca was selected by the Inventor as a flowering plant within the progeny of this cross in a controlled environment in Emerald, Victoria, Australia in 1995.

Plants of the new cultivar are different from plants of the female parent, the selection 92/18 in leaf size, ray floret color and inflorescence size. Plants of the new Dimorphotheca are larger and have narrower ray florets than plants of the male parent, the selection 93/94. In addition, plants of the new Dimorphotheca have purple-colored ray floret bases whereas plants of both parent selections do not have purple-colored ray floret bases.

Asexual propagation of the new cultivar by terminal cuttings at Emerald, Victoria, Australia, has shown that the unique features of this new Dimorphotheca are stable and reproduced true to type in successive generations.

SUMMARY OF THE INVENTION

The following traits have been repeatedly observed and are determined to be the unique characterictics of 'Purple Blush'. These characteristics in combination distinguish 'Purple Blush' as a new and distinct cultivar:

1. Upright and mounding growth habit.
2. Dark green leaves.
3. Freely branching habit.

4. White ray florets with purple bases which gives the appearance of a purple ring at the center of the inflorescence.
5. Numerous inflorescences per plant.
6. Relative tolerance to high temperatures.

The cultivar 'Purple Blush' has not been observed under all possible environmental conditions. The phenotype may vary somewhat with variations in environment such as temperature, daylength and light intensity, without, however, any variance in genotype.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new Dimorphotheca.

The photograph at the top of the sheet comprises a side perspective view of a typical flowering plant of 'Purple Blush'.

The photograph at the bottom of the sheet is a close-up view of a typical inflorescence bud, typical opening inflorescence, typical opened inflorescence, and upper and lower surfaces of typical leaves of 'Purple Blush'.

DETAILED BOTANICAL DESCRIPTION

The following observations, measurements and values describe 25-cm containers with three plants of the new cultivar grown for about nine to eleven weeks in Bonsall, Calif., under outdoor, full-sun conditions with day temperatures ranging from 21 to 35° C. and night temperatures ranging from 13 to 18° C.

Color references are made to The Royal Horticultural Society Colour Chart except where general terms of ordinary dictionary significance are used.

Botanical classification: *Dimorphotheca aurantiaca* cultivar 'Purple Blush'.

Parentage:

*Female, or seed, parent.*—Proprietary selection of *Dimorphotheca aurantiaca* identified as code No. 92/18.

*Male, or pollen, parent.*—Proprietary selection of *Dimorphotheca aurantiaca* identified as code No. 93/94.

Propagation:

*Type.*—By terminal cuttings.

*Time to initiate roots.*—About 12 to 18 days at 21° C.

*Time to develop roots.*—About 10 to 15 days at 21° C.

*Root description.*—Thick, fleshy and freely branching.

Plant description:

*Appearance.*—Perennial herbaceous container and garden plant. Upright and mounding growth habit; inverted triangle. Dark green foliage. Inflorescences held above and beyond the foliage on long peduncles. Freely branching with about 10 to 14 lateral branches; removal of terminaL apices (pinching) will enhance branching.

*Crop time.*—About 9 to 11 weeks are required to produce a finished, flowering plant in a 10-cm container.

*Vigor.*—Moderately vigorous.

*Plant height.*—About 34 cm.

*Plant spread.*—About 24 cm.

*Lateral branch description.*—Length: About 32 cm. Diameter: About 6 mm. Internode length: About 1 cm. Texture: Glabrous; stems thick and somewhat succulent. Color: 145A.

*Foliage description.*—Leaves alternate, single. Quantity of leaves per lateral branch: About 18. Length, fully expanded leaves, basal: About 8.5 cm. Width, fully expanded leaves, basal: About 2 cm. Shape: Elliptic. Apex: Acute. Base: Attentuate, sessile. Margin: Entire with irregularly-spaced teeth. Aspect: Mostly flat.

*Texture.*—Leathery and tough; slightly coarse; glandular; thick cuticle. Color: Young foliage, upper surface: 137A. Young foliage, lower surface: 137B. Fully expanded foliage, upper surface: Slightly darker than 137A. Fully expanded foliage, lower surface: 137B. Attentuated leaf base: 144A to 144B. Venation, upper surface: 138B. Venation, under surface: 138B.

Inflorescence description:

*Appearance/longevity.*—Daisy-type composite inflorescence form. Inflorescences displayed above and beyond foliage on long peduncles arising from leaf axils. Disc and Ray florets arranged acropetally on a capitulum. Typically about four buds and opened inflorescences per lateral stem. Inflorescences last about one week on the plant. Inflorescences persistent.

*Flowering response.*—Plants flower continuosly from April to October in the Northern Hemisphere,.

*Fragrance.*—None detected.

*Inflorescence size.*—Diameter: About 6 cm. Depth (height): About 1.3 cm. Diameter of disc: About 1.3 cm.

*Inflorescence buds.*—Length: About 2 cm. Width: About 1.1 cm. Shape: Pointed ovoid. Color: 144A.

*Ray florets.*—Quantity of ray florets per inflorescence: About 14 in a single whorl. Length: About 3 cm. Width: About 7 mm. Shape: Ligulate, elongated oblong. Apex: Slightly tri-dentate. Base: Acute. Margin: Entire. Aspect: Initially, slightly tilted upright; with development, somewhat reflexed. Texture: Smooth, satiny. Color: When opening, upper surface: 155D. When opening, lower surface, Longitudinal stripes, center, 138B; at margins, 144D and 142C; towards apex, 145A. Fully opened, upper surface: 155D; base, 70A. Fully opened, under surface: Longitudinal stripes, center, 138C to 138D; at margins, 144D.

*Disc florets.*—Quantity of disc florets per inflorescence: About 64. Shape: Tubular; five-lobed, fluted at apex. Length: About 8 mm. Width: About 3 mm at apex; about 1 mm at base, Color: Immature: 157B; apex, 145B. Mature: 157B.

*Phyllaries.*—Quantity per inflorescence and arrangement: About 13 per inflorescence; single whort, fused at base. Length: About 1.2 cm. Shape: Elliptic. Apex: Sharply acute. Margin: Entire. Texture: Slightly coarse. Color: Upper surface: 143A. Lower surface: 138A.

*Peduncle.*—Length: About 10.5 cm. Aspect: Moderately strong, erect to almost perpendicular to the vertical axis of the plant; inflorescences held above and beyond the foliage. Texture: Coarse; slightly pubescent and glandular. Color: 144A.

*Reproductive organs.*—Androecium: Present on disc florets only. Stamens: Five. Anther shape: Oblong. Anther size: About 2 mm. Anther color: 14A tipped with 79A. Pollen: Scarce to moderate. Pollen color: 14A. Gynoecium: Present on ray and disc florets. Pistils: One per floret. Pistil length: About 6 mm. Stigma shape: Bipartite. Stigma color: 83A. Style length: About 3 mm. Style color: 155D. Ovary color: 145D.

*Seed.*—Seed production has not been observed to date.

Disease resistance: Resistance to pathogens common to Dimorphotheca has not been observed on plants of the new Dimorphotheca.

High temperature tolerance: Plants of the new Dimorphotheca have been observed to be relatively tolerant to high temperatures.

It is claimed:

1. A new and distinct cultivar of Dimorphotheca plant named 'Purple Blush', as illustrated and described.

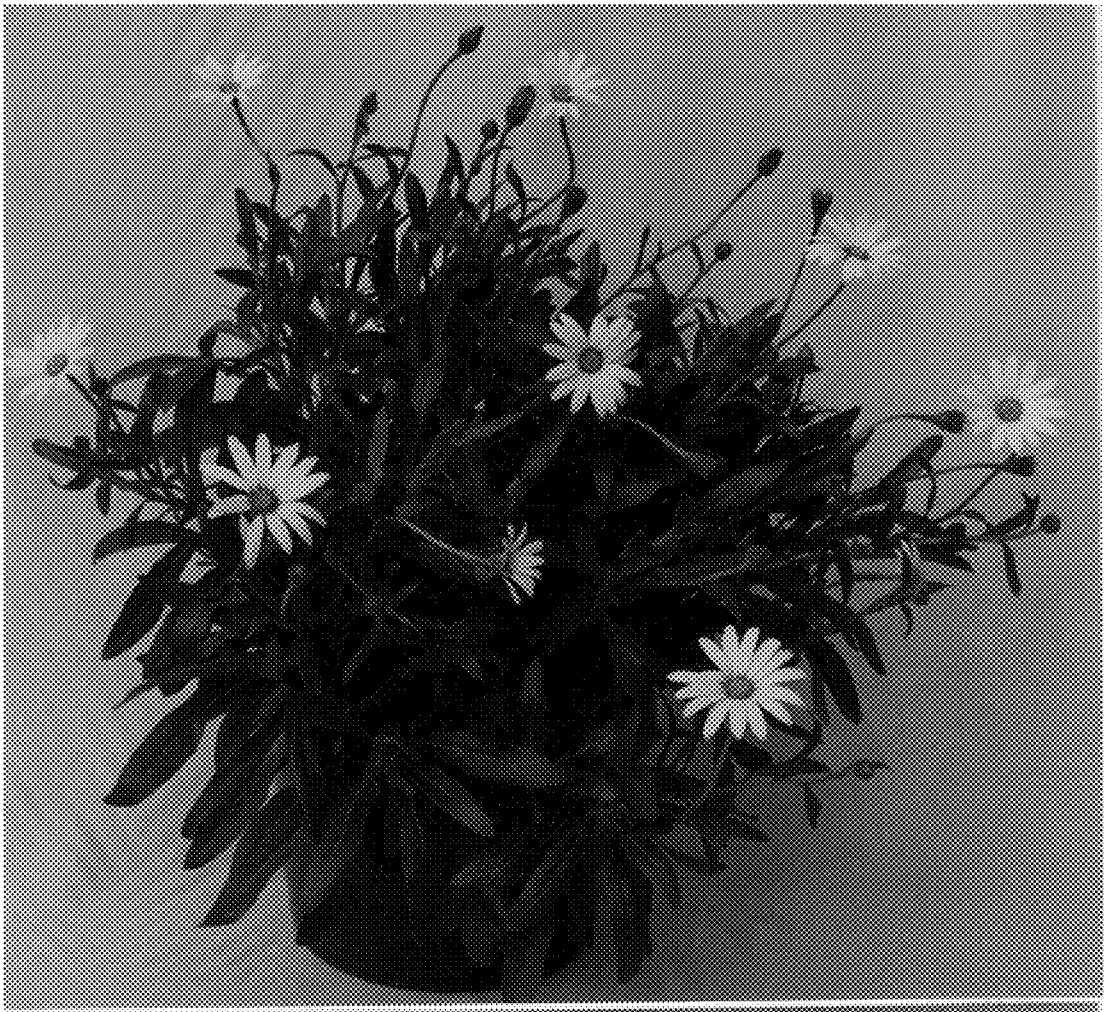
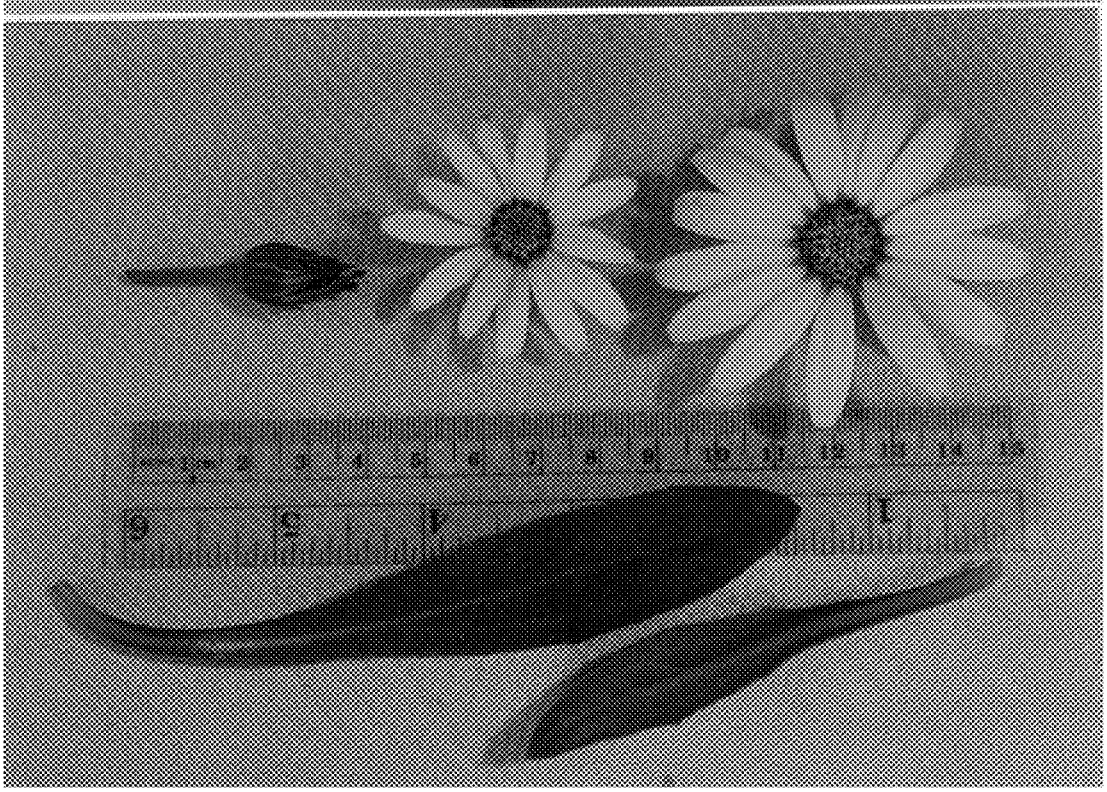

* * * * *